(12) United States Patent
DiFoggio et al.

(10) Patent No.: US 7,016,026 B2
(45) Date of Patent: Mar. 21, 2006

(54) METHOD AND APPARATUS FOR A DOWNHOLE REFRACTOMETER AND ATTENUATED REFLECTANCE SPECTROMETER

(75) Inventors: Rocco DiFoggio, Houston, TX (US); Arnold Walkow, Houston, TX (US); Paul Bergren, Houston, TX (US); Louis Perez, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/641,400

(22) Filed: Aug. 14, 2003

(65) Prior Publication Data

US 2004/0109156 A1    Jun. 10, 2004

Related U.S. Application Data

(63) Continuation-in-part of application No. 10/119,492, filed on Apr. 10, 2002, now Pat. No. 6,683,681.

(51) Int. Cl.
*G01N 21/41* (2006.01)
*G01N 21/35* (2006.01)

(52) U.S. Cl. ............... 356/128; 356/133; 356/134; 356/136; 250/339.12; 250/269.1

(58) Field of Classification Search ........ 356/128–137, 356/72–73; 250/269.1, 225, 265, 338.1, 250/339.1, 339.06, 339.12, 339.13, 341.8, 250/255

See application file for complete search history.

(56) References Cited

U.S. PATENT DOCUMENTS

| | | |
|---|---|---|
| 2,807,976 A | 10/1957 | Vossberg |
| 2,885,923 A | 5/1959 | Simmons |
| 3,770,352 A | 11/1973 | White |

(Continued)

FOREIGN PATENT DOCUMENTS

| | | |
|---|---|---|
| EP | 0116746 | 8/1984 |

(Continued)

OTHER PUBLICATIONS

A.R. Smits et al., "In-Situ Optical Fluid Analysis As An Aid To Wireline Formation Sampling", Society of Petroleum Engineers, SPE Formation Evaluation, Jun. 1, 1995, pp. 91-98.

(Continued)

*Primary Examiner*—Gregory J. Toatley, Jr.
*Assistant Examiner*—Sang H. Nguyen
(74) *Attorney, Agent, or Firm*—Madan, Mossman & Sriram, P.C.

(57) ABSTRACT

The invention relates to refractometry and attenuated reflectance spectrometry in a wellbore environment. Specifically, it pertains to a robust apparatus and method for measuring refractive index of fluids along a continuum (rather than in steps), and for measuring attenuated reflectance spectra, and for interpreting the measurements made with this apparatus to determine a variety of formation fluid parameters. The present invention provides a method and apparatus to distinguish between gas and liquid based on the much lower index of refraction of gas. It can also be used to monitor fluid sample clean up over time. The refractive index of a wellbore fluid is determined from the fraction, R, of light reflected off the interface between a transparent window that has a known refractive index and this fluid. Preferably, the refractive index is measured at some wavelength of light for which the fluid is not highly attenuating but is optimally attenuating. The adjacent transmission spectrometer can be used to correct the refractive index measurement for attenuation at those wavelengths, which it monitors. Also, this reflection-based refractometer design can be used as an attenuated reflectance spectrometer at highly attenuating wavelengths.

27 Claims, 10 Drawing Sheets

U.S. PATENT DOCUMENTS

| | | | |
|---|---|---|---|
| 3,869,208 A * | 3/1975 | Lorenz | 356/336 |
| 4,276,475 A * | 6/1981 | Nelson | 250/373 |
| 4,427,293 A * | 1/1984 | Harmer | 356/133 |
| 4,440,022 A * | 4/1984 | Masom | 73/293 |
| 4,540,285 A * | 9/1985 | Amer | 356/432 |
| 4,569,590 A | 2/1986 | Karny et al. | |
| 4,609,821 A | 9/1986 | Summers | |
| 4,699,516 A * | 10/1987 | Bartz et al. | 356/445 |
| 4,704,029 A * | 11/1987 | Van Heuvelen | 356/39 |
| 4,711,126 A * | 12/1987 | Houpt et al. | 73/293 |
| 4,745,293 A * | 5/1988 | Christensen | 250/577 |
| 4,803,470 A * | 2/1989 | Fineman | 340/583 |
| 4,834,533 A * | 5/1989 | Horike et al. | 356/133 |
| 4,844,608 A * | 7/1989 | Smith | 356/136 |
| 4,997,278 A * | 3/1991 | Finlan et al. | 356/128 |
| 5,028,139 A * | 7/1991 | Kramer et al. | 356/446 |
| 5,055,699 A | 10/1991 | Konig et al. | |
| 5,083,018 A * | 1/1992 | Rhyne | 250/227.25 |
| 5,166,747 A | 11/1992 | Schroeder et al. | |
| 5,167,149 A | 12/1992 | Mullins et al. | |
| 5,201,220 A | 4/1993 | Mullins et al. | |
| 5,241,859 A | 9/1993 | Smith | |
| 5,250,186 A * | 10/1993 | Dollinger et al. | 210/656 |
| 5,304,795 A * | 4/1994 | Fujihira et al. | 250/234 |
| 5,305,071 A | 4/1994 | Wyatt | |
| 5,325,170 A * | 6/1994 | Bornhop | 356/128 |
| 5,396,325 A * | 3/1995 | Carome et al. | 356/128 |
| 5,436,454 A * | 7/1995 | Bornstein et al. | 250/339.12 |
| H1470 H * | 8/1995 | Ewing et al. | 356/128 |
| 5,442,435 A * | 8/1995 | Cooper et al. | 356/133 |
| 5,680,043 A | 10/1997 | Hurlimann et al. | |
| 5,721,430 A * | 2/1998 | Wong | 250/339.13 |
| 5,939,717 A | 8/1999 | Mullins | |
| 5,946,084 A * | 8/1999 | Kubulins | 356/128 |
| 6,088,656 A | 7/2000 | Ramakrishnan et al. | |
| 6,130,439 A | 10/2000 | Le Menn | |
| 6,388,251 B1 * | 5/2002 | Papanyan | 250/269.1 |
| 6,465,775 B1 * | 10/2002 | Mullins et al. | 250/269.1 |
| 6,559,639 B1 | 5/2003 | Minh et al. | |
| 2002/0153888 A1 | 10/2002 | Kruspe et al. | |
| 2003/0231017 A1 | 12/2003 | Kiesl et al. | |

FOREIGN PATENT DOCUMENTS

| | | |
|---|---|---|
| JP | 61011636 | 1/1986 |
| WO | WO 03/016953 A1 | 2/2003 |

OTHER PUBLICATIONS

C.W. Morris et al., "Using Optical Fluid Analysis To Evaluate Downhole Fluid Sample Contamination", Society of Petroleum Engineers, SPE 50603, Oct. 20-22, 1998, pp. 283-295.

Jean M. Bennett, "Polarization" Handbook of Optics, vol. 1, Fundamentals, Techniques, and Design, Chapter 5, pp. 5.1-5.11.

* cited by examiner

METHOD AND APPARATUS FOR A DOWNHOLE REFRACTOMETER AND ATTENUATED REFLECTANCE SPECTROMETER

CROSS REFERENCE TO RELATED APPLICATIONS

This application is a continuation in part of and takes priority from U.S. patent application Ser. No. 10/119,492 filed on Apr. 10, 2002, now U.S. Pat. No. 6,683,681, by Rocco DiFoggio et al., entitled "A Method and Apparatus for Downhole Refractometer And Attenuated Reflectance Spectrometer" which is hereby incorporated herein by reference in its entirety.

FIELD OF THE INVENTION

The invention relates to refractometry and spectrometry in a wellbore environment. Specifically, it pertains to a robust apparatus and method for measuring refractive index of fluids along a continuum (rather than in steps), of measuring attenuated reflectance spectra, and to the interpretation of measurements made with this apparatus to determine a variety of formation fluid parameters. The refractometer and attenuated reflectance spectrometer disclosed here uses a simplified design, which is very appropriate for a downhole environment.

BACKGROUND OF THE INVENTION

Oil and gas companies spend large sums of money in their attempts to find hydrocarbon deposits. They drill exploration wells in their most promising prospects and use these exploration wells not only to determine whether hydrocarbons are present but also to determine the properties of those hydrocarbons, which are present.

For deep offshore fields, before any hydrocarbons can be produced, it is first necessary to spend several years building very expensive platforms with proper oil and gas handling facilities. The design specifications and cost of materials used in these facilities are strongly dependent on the properties of the hydrocarbons, such as gas to oil ratio, viscosity, bubble point pressure, asphaltene precipitation pressure, and so on. The exploration well itself is generally plugged and abandoned not long after it is drilled. However, the information that it provides is often used throughout the life of the oil or gas field.

To determine hydrocarbon properties, oil and gas companies often withdraw some hydrocarbons from the exploration well. Wireline formation testers, such as the Baker Atlas Reservoir Characterization Instrument (RCI) can be lowered into the well for this purpose.

Initially, fluids that are withdrawn may be highly contaminated by filtrates of the fluids ("muds") that were used during drilling. To obtain samples that are sufficiently clean (usually <10% contamination) so that the sample will provide meaningful lab data concerning the formation, formation fluids are generally pumped from the wellbore for 30–90 minutes, while clean up is being monitored in real time. Then, these withdrawn fluids can be collected downhole in tanks for subsequent analysis in a laboratory at the surface.

Alternatively, for some properties, samples can be analyzed downhole in real time. The present invention relates both to monitoring sample clean up and to performing downhole analysis of samples at reservoir conditions of temperature and pressure.

A downhole environment is a difficult one in which to operate a sensor. Measuring instruments in the downhole environment must operate under extreme conditions and limited space within a tool's pressure housing, including elevated temperatures, vibration, and shock.

U.S. Pat. No. 5,167,149 by Mullins et al. and U.S. Pat. No. 5,201,220 by Mullins et al., are both entitled Apparatus and Method for Detecting the Presence of Gas in a Borehole Flow Stream. The Mullins apparatus of that invention comprises a downhole 8-channel critical angle (and Brewster angle) refractometer to distinguish oil from gas and to estimate the percentage of gas in a fluid.

The traditional method of measuring the index of refraction of a dark fluid (such as a crude oil) is the critical angle refractometer. A diverging beam of light travels through a transparent solid (e.g., glass) and strikes the interface between this transparent solid and some fluid to be measured, which is in contact with the transparent solid. The reflected diverging beam is dimmer at those angles, which are close to a normal to the interface. At such angles, some of the light is transmitted (refracted) into the fluid.

The reflected diverging beam is much brighter at glancing angles. Starting at the Brewster angle, any incident p-polarized light suffers no reflection loss. Starting at the critical angle, all light, regardless of polarization, suffers no reflection loss but is 100% reflected from the interface so that no light is transmitted into the fluid.

The critical angle can be calculated from Snell's Law, $n_0 \sin \theta_0 = n_1 \sin \theta_1$, for light refracted as it travels from medium $n_0$ to medium $n_1$. The maximum possible refracted angle (as measured from the normal to the interface) is 90° so by substituting $\theta_1 = 90°$ into Snells's Law we can calculate the critical angle, $\theta_c = \arcsin(n_1/n_0)$.

At the critical angle, we see a large change in reflected intensity (a bright/dark demarcation), which can be located using a single moveable detector or an array of stationary photodetectors. A single moveable detector would add substantial mechanical complications to a downhole design.

Laboratory instruments often use an array of 1024 or more stationary photodetectors to detect the critical angle. However, mimicking the lab design downhole would be difficult because multiplexers built into photodetector arrays generally do not work above about 95 C. Even with separate high-temperature multiplexers, multiplexing so many very weak signals at the elevated temperatures encountered downhole would be problematic as they would probably have to be stacked to reduce noise. Therefore, downhole, only a few fixed photodetector elements (e.g., 8) are likely to be used for a critical angle refractometer. Of course, with an 8-channel refractometer, as described in U.S. Pat. Nos. 5,167,149 and 5,201,220 mentioned earlier, the refractive index is measured only in 8 steps rather than as a continuum.

Because such a device only measures refractive index in eight coarse steps, it would be difficult for an operator of this device to monitor sample clean up. Sample clean up refers to the transition from filtrate-contaminated fluid to nearly pure formation fluid while pumping fluid from selected depths in the wellbore.

Accurate sample clean up monitoring cannot be provided by processing a course refractive index reading. Thus, there is a need for a method and apparatus, which can measure refractive index along a continuum so that an operator can accurately monitor the refractive index of a formation sample.

SUMMARY OF THE INVENTION

The present invention provides a continuous refractive index measurement. An advantage to monitoring clean up by using a continuous refractive index measurement is that refractive index is much less sensitive to the passage of sand or other particulates, which can cause sudden spurious increases ("jumps") in absorbance across the entire spectrum of a downhole transmission spectrometer. The depth of investigation in the sample is only 1–2 microns from the sapphire window surface into the sample, thus the optical measurements for the sample are not affected by gas bubbles or particles more than 3 microns from the window surface. The narrow depth of investigation is referred to as an interface technique because only a very shallow depth (1–2 microns) is investigated in the sample. Thus, the interface technique provided by the present invention substantially eliminates temporary increase in brightness caused by a gas bubbles and temporary increase in darkness caused by particles because most bubbles and particles that do not pass within 1–2 microns of the sapphire window surface. Interestingly, lines 17–23 of column 5 in U.S. Pat. No. 5,166,747 specifically state, "reflection due to the interface of the sapphire wall and the liquid sample does not provide useful information" which teaches away from the present invention.

The refractometer of the present invention is less sensitive to particulates because it probes the fluid to a depth of only a few wavelengths of light past the window so it does not see all of the particulates that pass through the 2-mm pathlength cell (304). Few particles get within a few wavelengths of light of the window, in part, because there is a coating of fluid around the particles and around the window that is at least a few wavelengths of light.

The present invention does not require measuring the critical angle. Furthermore, it can also be used as an attenuated reflectance spectrometer.

The present invention provides a continuous refractive index measurement and comprises an apparatus and method of simplified refractometer design for durable and accurate operation in a downhole environment. In one aspect of the invention, the present invention provides for novel interpretation of measurements made with the refractometer of the present invention. In another aspect of the invention, the present invention provides a method and apparatus to distinguish between gas and liquid based on the much lower index of refraction of gas. In another aspect of the invention, the present invention provides a method for determining the refractive index of a wellbore or formation fluid from the fraction of light, R, reflected off of the interface between a transparent window and the wellbore or formation fluid. In another aspect of the invention, the present invention can be used to observe the bubble point and dew point of formation fluid during depressurization, or to provide accurate determination of a number of other formation properties. In another aspect of this invention, the present invention can be used to obtain a fluid's absorption spectra in highly attenuating regions.

Highly attenuating regions include the asphaltene peak (due to electronic transitions) in the visible and near infrared or strong molecular vibrational peaks in the mid-infrared (whose absorbance can be over a 100 times greater than corresponding absorbance peaks in the near infrared) or in the near infrared. Such spectra are, in general, too attenuating to be measured using transmission spectroscopy over a 2-mm pathlength.

The mid-infrared is often called the "fingerprint" region of infrared spectroscopy because it is where subtle chemical differences can often appear particularly obvious. Infrared spectra of alkanes (found in crude oils) are different from the spectra of alkenes (found only in certain drilling fluids) or the spectra of various aromatics (founds mostly in crude oils but absent, by design, from any environmentally-friendly synthetic drilling fluids).

Infrared spectral differences can form the basis for an improved method to estimate the amount of drilling fluid contamination in a sample based on subtle differences in chemical composition inferred from molecular vibrational spectroscopy rather than color. These, and other objects and advantages of the invention, will be evident from the following example of a preferred embodiment, which is disclosed in the Detailed Description of the Invention.

DETAILED DESCRIPTION OF THE INVENTION

The present invention provides a method and apparatus for determining a number of formation fluid properties from a refractometer measurement. The present invention also provides a method and apparatus to more accurately distinguish between gas and liquid based on the much lower index of refraction of gas. The refractive index of a wellbore or formation fluid can be determined from the fraction of light, R, reflected off of the interface between the preferred transparent window, having a known refractive index and the formation fluid under analysis.

Figure 1:
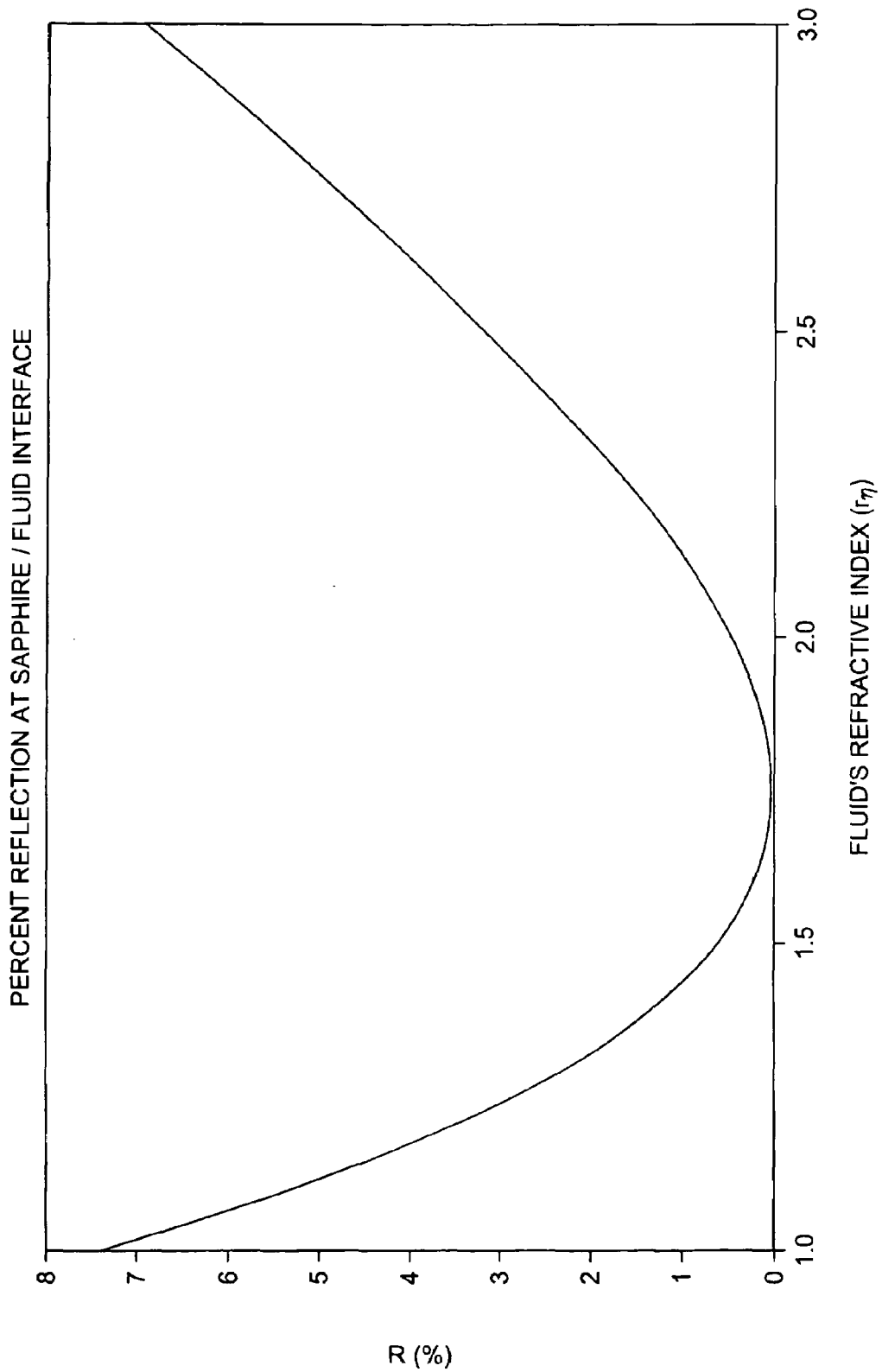
FIG. 1 shows the percentages of light reflected at a fluid/sapphire interface versus the index of refraction for normal incidence (perpendicular) to the interface, where the fluid is the refractive medium being measured.

FIG. 1 shows the percentage of light reflected from the fluid/sapphire interface, when that light is incident perpendicular to the plane of the surface of the transparent window and interface. In this figure, the window has a fixed index of refraction of 1.75 but the index of refraction of the fluid varies. The minimum reflection occurs when the fluid's refractive index equals the window's refractive index, which for sapphire, is 1.75.

Figure 2:
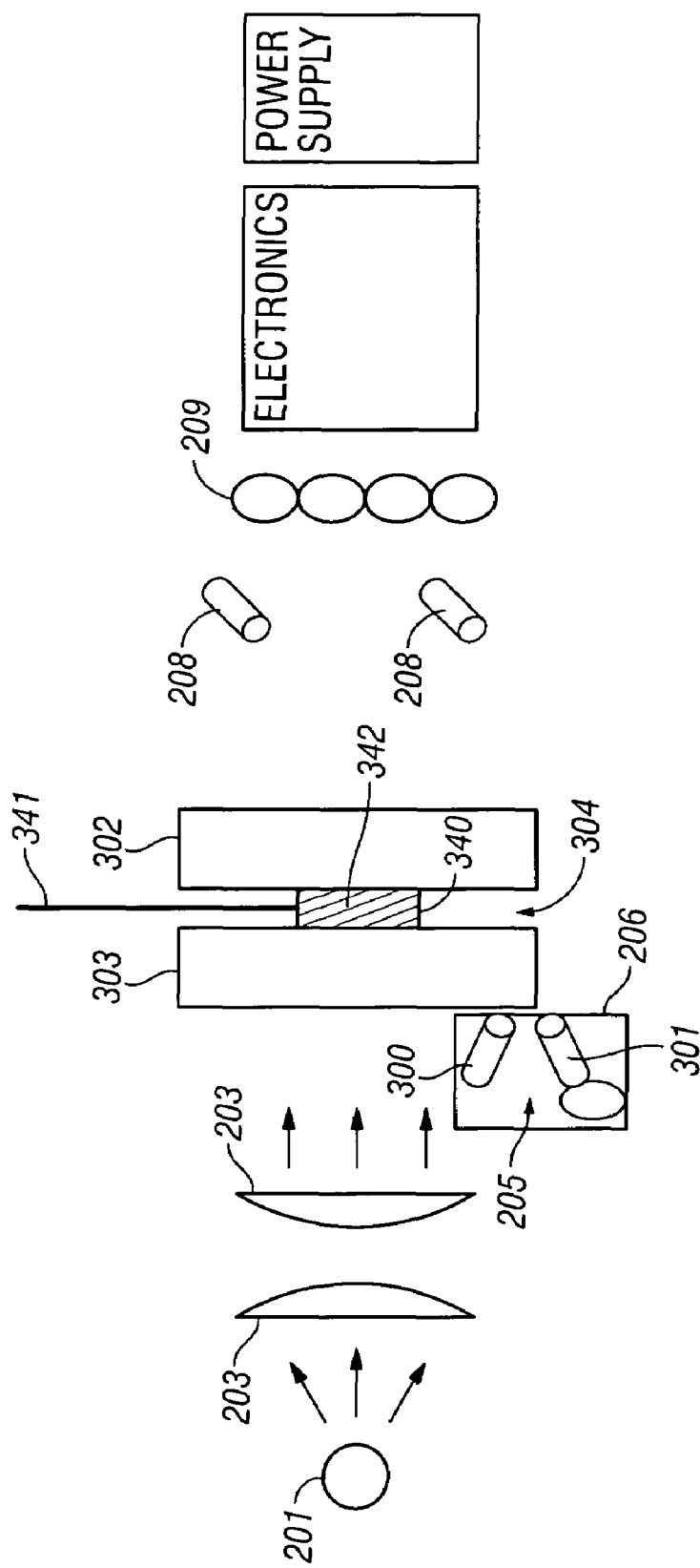
FIG. 2 is a diagram of a preferred embodiment of the refractometer of the present invention.

FIG. 2 shows a preferred refractometer design of the present invention that fits into the existing space within a downhole fluid-characterization tool, which can perform in situ analysis of formation and wellbore fluids (for example, a Baker Atlas SampleView$^{SM}$ tool).

In a preferred embodiment, a light source 201 (e.g. a tungsten light bulb) emits light toward a formation or wellbore fluid sample. The emitted light is collimated by a collimating lens device 203, which lies between the light source and the fluid sample. If unimpeded, the collimated light beam is incident generally perpendicular to the exterior surface of a first sapphire window 303. Sapphire windows 303 and 302 lie generally perpendicular to the collimated beam of light and are separated by a gap or channel 304 enabling a fluid under analysis to flow between them. In a preferred embodiment, the refractometer assembly 205 diverts a portion of the incident collimated beam from 310 and focuses it onto interface 307 between the first sapphire window 303 and the fluid in channel 304. The reflected light beam is split at 317 between a refractometer (316, 318, and 320) and an attenuated reflectance spectrometer, 321. That portion of the collimated light beam, which is not diverted for use in the refractometer or the attenuated reflectance spectrometer continues on for use in other experiments such as a transmission absorption spectrometer, 209.

Figure 3:
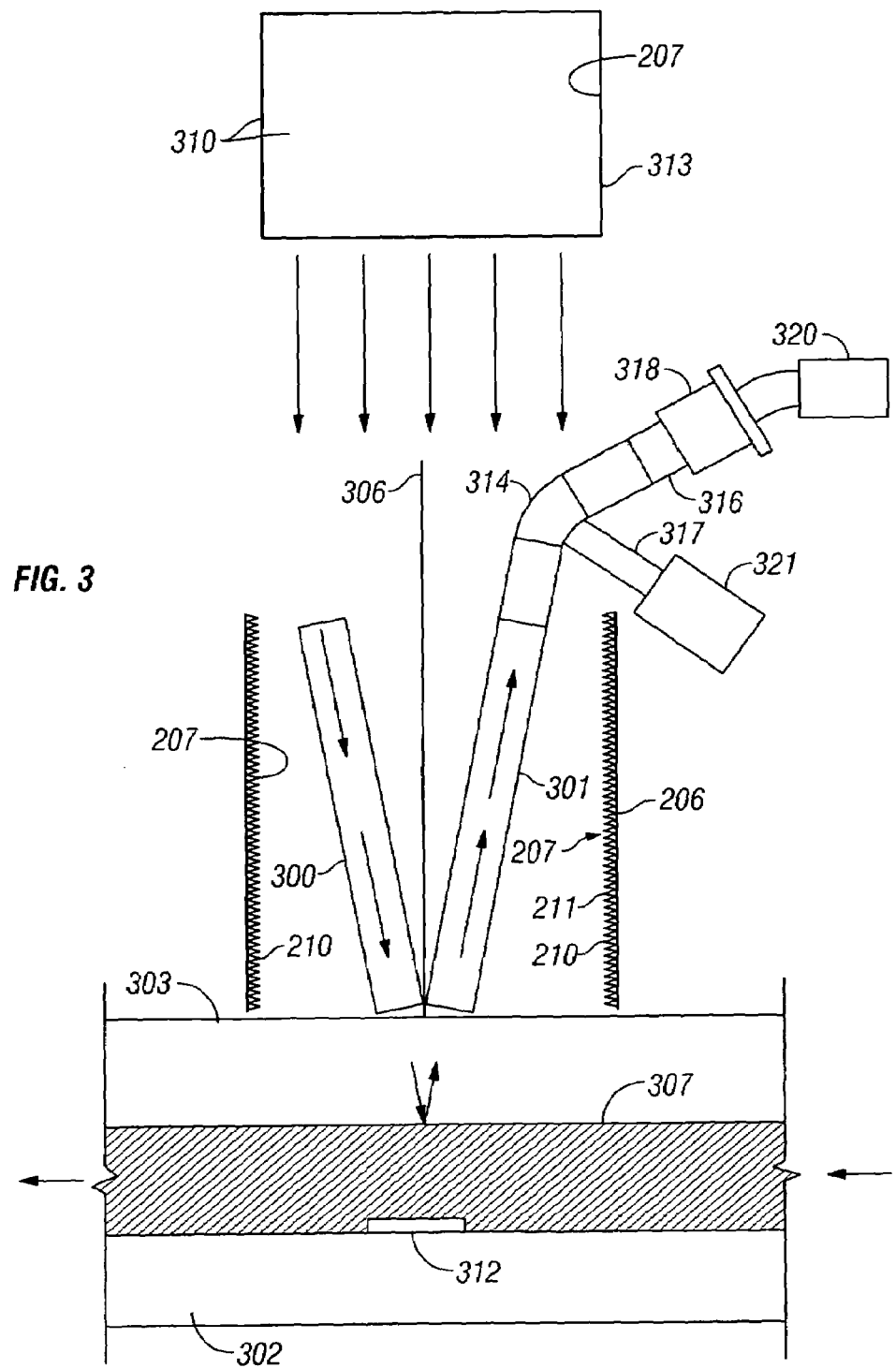
FIG. 3 is an expanded view of the refractometer of FIG. 2.

FIG. 3 is an expanded view of the refractometer assembly 205, which shows two optical transmission rods 300, 301 (which can be relay lenses or could simply be glass or sapphire rods) referred to as the left rod 300 and the right rod 301. The longitudinal axes of the two optical transmission rods lie in a plane perpendicular to the plane of both of the pressure containment plates 303, 302 comprising a first sapphire window 303 and a second sapphire window 302 and the channel 304. In addition, the two optical transmission rods 300, 301 are preferably side-by-side (and contacting each other where they meet 303) and may also be in contact the first sapphire plate 303. To maximize the light signal, we could apply a high-temperature index matching gel to bridge the gap between transmission rods 300, 301 and first sapphire plate 303. Leaving the gap unfilled except for air does not change the refractive index measurement because it diminishes the light intensity measurements of both the unknown and the reference sample by the same factor. Eq. 16, which is used to calculate the refractive index depends only on the ratio, $I_{r\_air}/I_{r\_unk}$, so a common factor in both numerator and denominator cancels out. Transmission rods 300 and 301 are preferably at equal angles (of about 4°) with respect to the normal and straddling the perpendicular centerline 306. These preferred angles are the minimum practical working angles that could be achieved within mechanical design constraints. The ideal angle would be zero degrees because that is what is assumed in our formula for calculating refractive index from reflected intensity. However, theoretical calculations show that the reflected intensity changes only negligibly (by −0.0062% for air and by −0.0079% for oil) going from 0° to 4°. When these reflection intensity errors are propagated through our formula, we find that our 4° angle causes an error in our measured index of refraction of oil referenced against air, that is a negligible 2 to 3 parts per million lower than it should be. The depth of investigation in the sample is only 1–2 microns from the sapphire window surface into the sample, thus the optical measurements for the sample are not affected by gas bubbles or particles more than 3 microns from the window surface. The narrow depth of investigation is referred to as an interface technique because only a very shallow depth (1–2 microns) is investigated in the sample. Thus, the interface technique provided by the present invention substantially eliminates temporary increase in brightness caused by a gas bubbles and temporary increase in darkness caused by particles as most all bubbles and particles do not pass within 1–2 microns of the sapphire window surface.

The preferred refractometer is calibrated by placing a substance with a known index of refraction (e.g. air or water) within the channel 304. The intensity of the reflected light transmitted to the first sapphire plate 303 via left rod 300 and reflected back through right rod 301 at this sapphire/air (or sapphire/water) interface is recorded and is used as the calibration reference value for calculating the index of refraction of other fluids from their relative reflection intensities. With a fluid having a known index (preferably air) in the channel 304 light source 310 is turned on, light enters the left rod 300, and reflects off of the fluid sapphire interface and back up through the right rod 301. This reflected light proceeds up a fiber optic link 314 to optical filter 316, and on to electro-optical transducer 318 and finally on to the electronic analysis/display system 320.

When using a known reference fluid that is transparent, a black test target 312 resides inside the channel 304 on the inside surface of the second sapphire window 302. It absorbs any light that passes through the first sapphire window and strikes the second sapphire window, thus eliminating back reflections from the second window 302. This test target 312 enables a correct reading, because removing target 312 would potentially allow back reflections from the second sapphire window 302 that could significantly add to and thus alter calibration readings. These secondary reflections, however, are generally a problem only in calibration. One reason is that the formation fluid generally has a higher absorbance than a reference fluid (air) used in calibration so secondary reflections are generally extinguished by the fluid itself. Another reason is that the fraction of light reflected at the first window fluid interface depends only on the refractive index of whatever fluid is within about one skin depth of that interface and the gap 304 is much larger than the skin depth.

In a preferred embodiment, formation fluid or gas is passed through channel 304 between the sapphire windows 302 and 303 and a reflected light intensity is measured. The reflected intensity depends primarily on the index of refraction of the thin layer of formation fluid in the channel 304 in contact with the upper plate interface 303.

The fiber optic link 314 enables the electro-optical transducer 318 and associated mounting apparatus to be situated outside of the central light beam, which is used for the transmission absorption spectrometer 209. The placement of the assembly prevents a shadow from being cast onto the portion of the sapphire window that can be used for other measurement such as transmission absorption spectroscopy 209.

Basic equations for reflection are well known and can be found, for example, in *Handbook of Optics, Volume I, Second Edition,* Michael Bass. ed. For a non-absorbing window and non-absorbing fluid, the reflection coefficient of a light beam perpendicular to the interface is given by, $$R = I_r/I_0 = (n_0 - n_1)^2/(n_0 + n_1)^2 \qquad (1)$$

where $n_0$ is the index of refraction of the window and $n_1$ is the index of refraction of the fluid. Equation 1 can be inverted to solve for $n_1$.

$$\text{For } n_1 < n_0, \; n_1 = n_0(1 - Sqrt(R))/(1 + Sqrt(R)) \qquad (2)$$

$$\text{For } n_1 > n_0, \; n_1 = n_0(1 + Sqrt(R))/(1 - Sqrt(R)) \qquad (3)$$

The invention preferably uses sapphire ($n_0 = 1.746$) for transmissive window material. The index of refraction of most crude oils is between approximately 1.43 and 1.55. The index of refraction of natural gas at high pressure is considerably less. Therefore, an implementation of this invention utilizes the formula associated with the case, $n_1 < n_0$ (Eq. 2). For light transmitted through the sapphire window and striking the fluid/window interface, the brighter the reflection from the interface, the lower the index of refraction of the fluid. The lowest fluid index of refraction is for vacuum ($n_0 = 1.0$), which is close to the index of refraction of air at one atmosphere of pressure ($n_0 = 1.0002926$) at 0° C.

The present invention further comprises correcting the estimation of the refractive index formula (Eq. 1) by accounting for any light absorption by the fluid (attenuated reflection effects) that occurs within approximately one skin depth of the fluid-window interface. Only when the fluid is highly attenuating at the wavelength of light used by the refractometer will the fluid absorb enough light within the short distance of one skin depth that it is necessary to correct for absorption by using Eq. 11 instead of the simpler Eq. 2.

The refractometer of the present invention is based on the intensity of light reflected at the sapphire/fluid interface.

Elimination of stray light is critical to successful operation of this type of refractometer. To that end, the present invention provides dull (not shiny) black coatings, such as matte-finish black chrome 207, at various places inside the tool such as the tube 206 within which the refractometer assembly sitsand the light source 310 housing 313. Prior to applying the black matte coating, a 210 thread is formed the inside of this tube 206 with a spiral pattern of threads that come to an apex 211(no plateaus) to further reduce any stray light from reflections within the tube.

The present invention also substantially eliminates reflections from the second sapphire window. To that end we interpose a black Teflon target surrounded by black chrome between the two windows. This exposes some black chrome to wellbore fluids and the black chrome seems to hold up moderately well. However, for the most critical spot in the wellbore fluid, we use rough-sanded carbon-loaded black Teflon because, unlike a coating, its blackness cannot be abraded off by particulates in the fluid. Any abrasion simply exposes more black Teflon. The black chrome is used in areas inside of the tool to reduce stray light in areas, which not expose well bore fluid.

To eliminate stray light from reflections off components that are beyond the second sapphire window is preferable to use a wavelength (1740 nm) that is somewhat (but not excessively) absorbing for both water and oil, i.e., "optimally absorbing". For the refractometer, we do not want to use a wavelength at which crude oils are highly absorbing (400–1100 nm asphaltene peaks) because then there would be substantial attenuated reflectance that would cause systematic errors in the refractive index readings for which we could not easily correct.

For a non-absorbing window and an absorbing fluid, a complex index of refraction of the fluid can be defined as a real part ($n_1$ prime) and an imaginary part ($k_1$).

$$n_1' + i k_1 \qquad (4)$$

where $$k_1 = (\alpha \lambda)/(4\pi) \qquad (5)$$

Here, $k_1$ is the imaginary part of the complex index of refraction of the fluid, representing absorption at wavelength $\lambda$, and $\alpha$ is the reciprocal of the distance (often called the "skin depth" or the "penetration depth") within which the light intensity falls to 1/e of its initial value. By the definition of absorbance, $A = \log_{10}[I_0/I]$. Multiplying both sides of this equation by a and replacing I by $(I_0/e)$, produces the corresponding absorbance per unit length in the fluid at wavelength, $\lambda$, as, $$A\alpha = \alpha \log_{10}[I_0/(I_0/e)] = \alpha \log_{10}(e) \qquad (6)$$

The absorbance, A, of the fluid over a fixed path length, L, is obtained through another procedure of the instrument. This length, L, is preferably chosen to be 2 mm. Absorbance per unit length is an intensive property (independent of shape or volume) of a fluid, similar to mass density. Thus, one can equate the measured absorbance per unit length, (A/L) to the right side of Equation (6) and solve for $\alpha$ to obtain the following equation:

$$\alpha = A/[L \log_{10}(e)] \qquad (7)$$

We can now substitute $\alpha$ from Eq. 7 into Eq. 5 to calculate $k_1$ in terms of the measured absorbance per unit length at wavelength, $\lambda$, as, $$k_1 = (A \lambda)/(4 \pi L \log_{10}(e)) \qquad (8)$$

Numerically, for L=2 mm, and $\lambda$ in nm, $$k_1 = A_{2\,mm} \lambda[nm]/(10\,915\,011) \qquad (9)$$

so, for 1300 nm, $k_1 = A_{2\,mm}/8396$; and for 1600 nm, $k_1 = A_{2\,mm}/6821$, where $A_{2\,mm}$ is the absorbance measured by our existing downhole transmission spectrometer next to which this refractometer will be installed.

For a non-absorbing window but absorbing fluid, the reflection coefficient of a light beam that is perpendicular, or nearly perpendicular, to the interface is given by, $$R = [(n_0 - n_1)^2 + k_1^2]/[(n_0 + n_1)^2 + k_1^2] \qquad (10)$$

We solve for $n_1$ to obtain $$n_1 = (n_0/a)\{1 \pm Sqrt\,[1 - a^2(1 + (k_1/n_0)^2)]\} \qquad (11)$$

where $a = (1-R)/(1+R)$. To minimize the need for an absorbance correction, measurement of the reflection coefficient is can be performed at wavelengths that are minimally absorbed by the fluid, such as 1300 nm and 1600 nm. These two wavelengths lie between the molecular absorbance bands. Preferably measurement is performed at 1740 nm because this wavelength is moderately (and optimally) absorbing for both oil and water and reduces stray light reflected from the far sapphire window.

Of course, crude oils also have electronic absorption bands that decline with increasing wavelength due to asphaltenes. For a light crude oil, the asphaltene peak often declines to a minimal absorbance by 1300 nm. For a medium gravity crude oil, the asphaltene peak may not decline to a minimal absorbance until the longer wavelength, 1600 nm. For a heavy crude oil, correction formulas (Eq. 9 and Eq. 11) may be needed to calculate $n_1$, despite using an minimally absorbing longer wavelength, such as 1600 nm. The spurious influence of asphaltene absorbance is even less at 1740 nm.

For normal incidence, at a wavelength where the fluid is not strongly absorbing, the following formula can be used to calculate the index of refraction, $n_{unk}$, of an unknown fluid. It calculates, $n_{unk}$, in terms of 1) the index of refraction of sapphire, 2) the index of refraction of air, 3) the ratio of the intensity of light reflected off the sapphire/air interface to the intensity of light reflected off of the sapphire/unknown interface.

$$n_{unk}=n_{sap}(a-b)/(a+b) \quad (14)$$

where $$a=(n_{sap}+n_{air})/(n_{sap}-n_{air}) \quad (15)$$

$$b=Sqrt(I_{r\_unk}/I_{r\_air}) \quad (16)$$

$I_{r\_air}$=Intensity of Reflected Signal when Air is in the cell
$I_{r\_unk}$=Intensity of Reflected Signal when an Unknown Fluid is in the cell
$n_{unk}$=Index of Refraction of Unknown Fluid
$n_{air}$=Index of Refraction of Air (is approximately 1.0029)
$n_{sap}$=Index of Refraction of Sapphire (is approximately 1.746)

Eq. 14 can be derived from Eq. 1 by taking the square root of the ratio of the reflectance for an unknown/sapphire interface to the reflectance for an air/sapphire interface, then applying the definitions of a and b, and finally, solving for $n_{unk}$.

Figure 4:
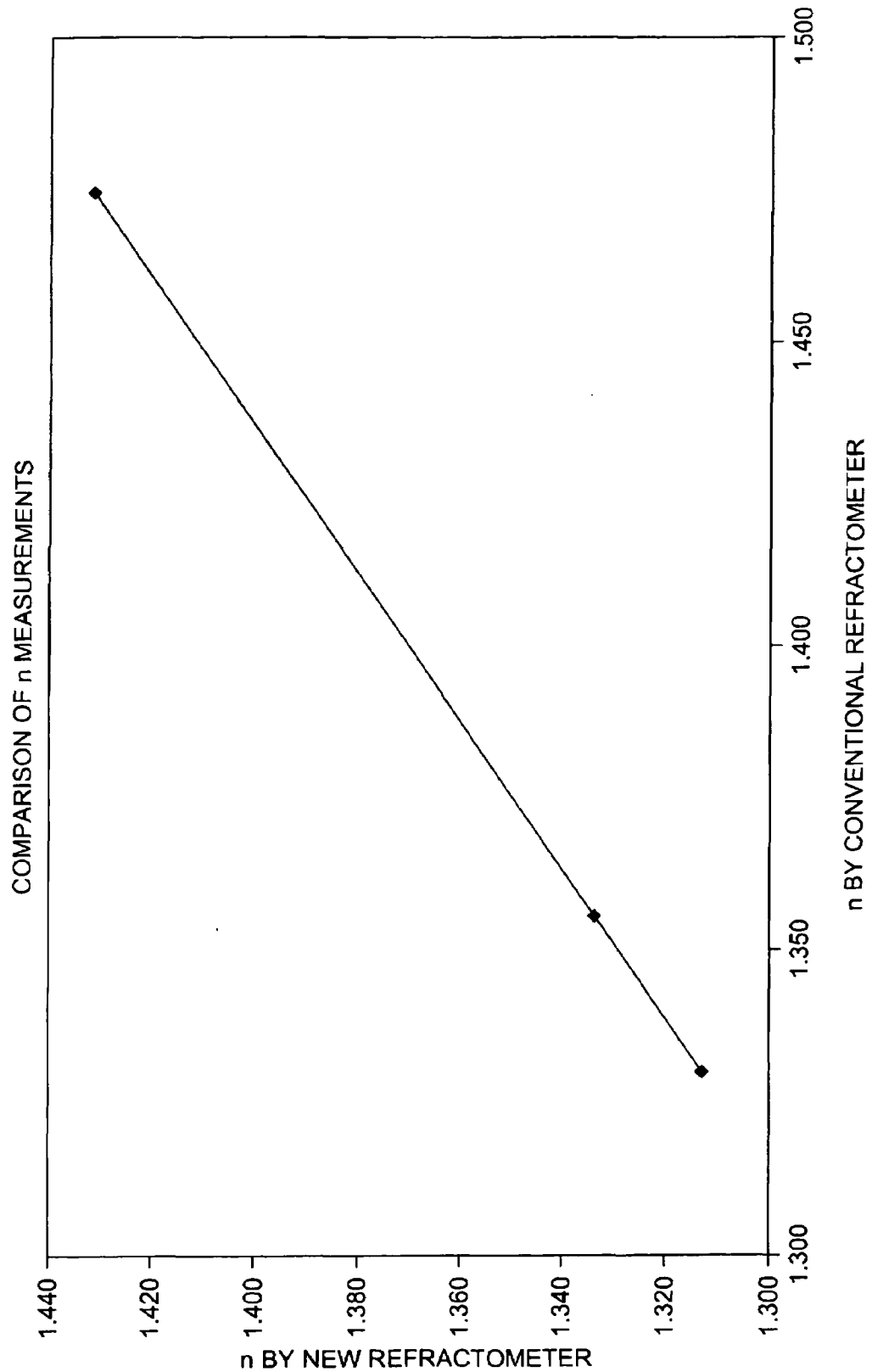
FIG. 4 is a graph comparing readings of the present-invention spectrometer to readings of a known spectrometer.

FIG. 4 compares the refractometer of the present invention measurements of refractive indices (at 1600 nm using Eq. 14) to refractive indices measured in the visible with a conventional refractometer for water, pentane, and tricloroethane (low, medium, and high refractive index, respectively). Further refinements could be made to correct for slight changes in the refractive indices of air and sapphire with temperature or to correct refractive indices (measured at 1600 nm by the present invention) to conventional indices (measured in the visible, often at 589 nm).

The present invention obtains crude oil spectra over the highly attenuating asphaltene peak in the visible and short wave near infrared. A reference spectrum of reflected intensity versus wavelength was collected by attaching a small Ocean Optics S2000 portable fiber optic spectrometer directly to fiber optic link 314 and over the range of 400–1100 nm when air was the fluid filling the gap 304 under the first sapphire window 303. The gap 304 was then filled with crude oil and the present invention collected another spectrum of reflected intensity versus wavelength. The base ten log of the ratio of these two spectra generated the crude oil's absorbance spectrum over the asphaltene region. This measurement displayed asphaltene's characteristic rising absorption at shorter wavelengths.

To use the present invention as both a refractometer and an attenuated reflectance spectrometer, an optical splitter 317 is added to fiber optic link 314. The splitter 317 sends part of the collimated light beam to the original optical filter 316 and to the electro-optical transducer 318 of the refractometer. The splitter diverts the rest of the beam to an attenuated reflectance spectrometer 321 comprising one or more optical filters, gratings, or other wavelength-separating components and photodectectors.

Figure 5:
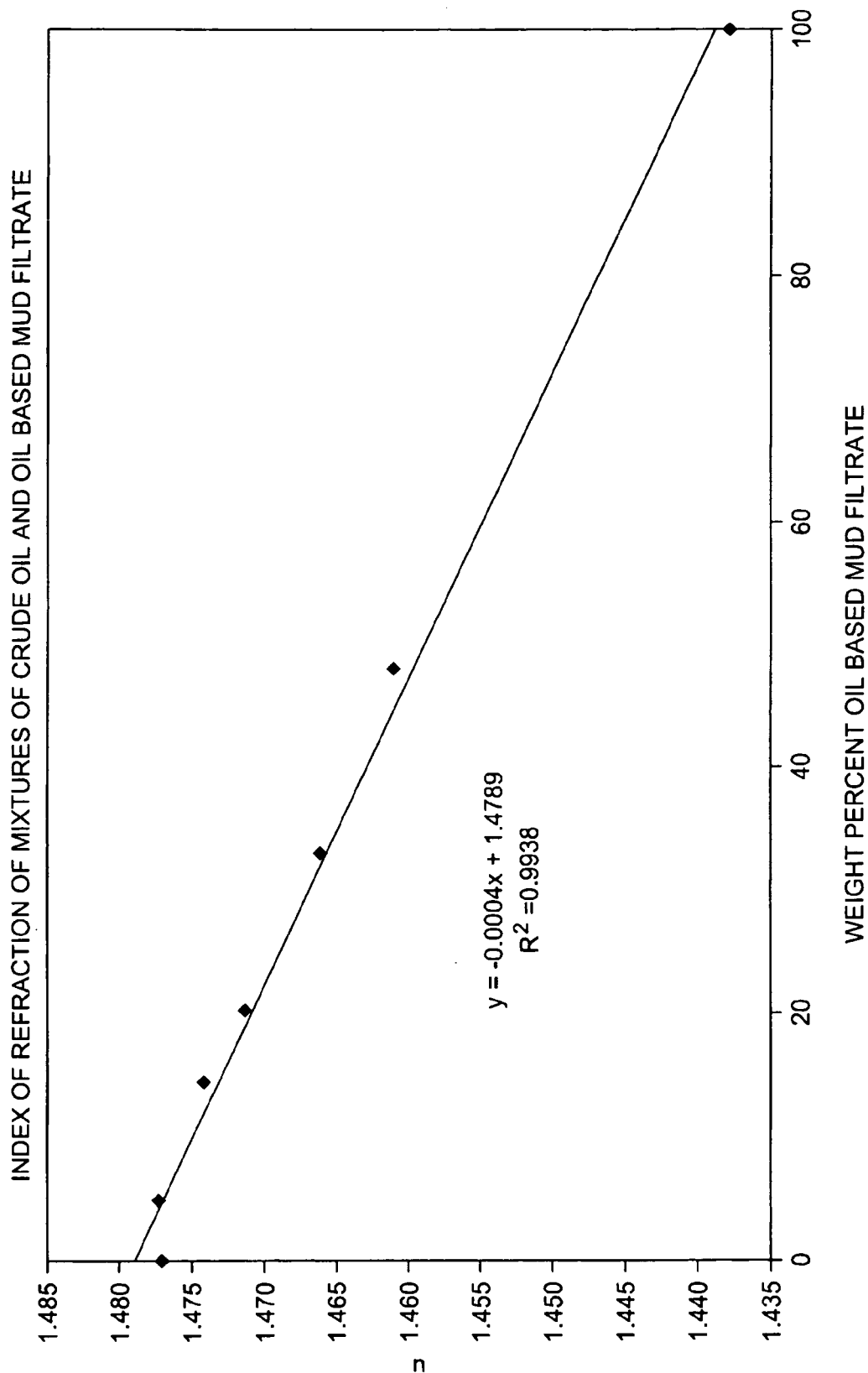
FIG. 5 is a graph showing the change in measured refractive index, n, of a contaminated crude oil with the percentage of oil based mud filtrate contamination.

The present invention provides a continuum of refractive index readings (rather than coarse steps), thus, the continuous refractive readings can also be used to monitor more subtle changes in the refractive index such as those associated with sample clean up. Sample clean up refers to the transition from filtrate-contaminated formation fluid to nearly pure formation fluid while pumping fluid from selected depths in the wellbore. FIG. 5 illustrates how the refractive index of a contaminated crude oil can be related to the percentage of oil based mud filtrate contamination.

The Clausius-Mossotti equation (Eq. 17) relates the Clausius-Mossotti ratio, $r=(n^2-1)/(n^2+2)$, to the mass density, $\rho$, and molar polarizability, P, and the gram-molecular weight, M.

$$(n^2-1)/(n^2+2)=\rho P_m/M \quad (17)$$

For an ideal mixture, the volumetrically weighted sum of the each component's Clausius-Mossotti ratio is equal to the mixture's Clausius-Mossotti ratio. In this way, one can relate the index of refraction of a mixture to the index of refraction of its constituent components. For an ideal mixture, the volumetrically weighted sum of the each component's Clausius-Mossotti ratio is equal to the mixture's Clausius-Mossotti ratio. In this way, we can relate the index of refraction of a mixture to the index of refraction of its constituent components. That is, if a mixture's index of refraction is n, and the i-th component of the mixture occupies a volume fraction, fi, and has an index of refraction, ni, then, $$(n^2-1)/(n^2+2)=\Sigma_i f_i(n_i^2-1)/(n_i^2+2) \quad (18)$$

The present invention also enables determination of the dew point pressure for fluid in the channel, which if pure formation fluid, represents the fluid in the surrounding formation. By capturing a sample of formation fluid in the channel 304 and changing the volume by closing valve 340 and moving the piston 341 up or down to decrease or increase the volume of the sample in channel 304 and increase or decrease the pressure in channel 304 respectively, the present invention enables a user to determine the dew point or bubble point for the fluid sample 340. The present invention measures the refractive index of fluid within a short distance into the sample, past the interface, the span of a few wavelengths of light from the channel/sample interface. At the dew point, gas preferentially condenses to liquid on solid surfaces, which act as nucleation sites. That is, at the dew point, a sheet of liquid forms on the window and is detected by the present invention using the change in refractive index detected when going from a gas to a liquid.

The measured index of refraction rises during a fluid's transition from a gaseous phase to a liquid phase because, with a liquid phase in contact with the window, there is a drop in the intensity of the reflected light. However, in the unlikely event that the thin liquid layer is perfectly flat and parallel rather than slightly wedge shaped, some of the reflection from the fluid/gas interface can make it back to the detector, resulting in a less dramatic change in reflected light when crossing the dew point.

Figure 6:
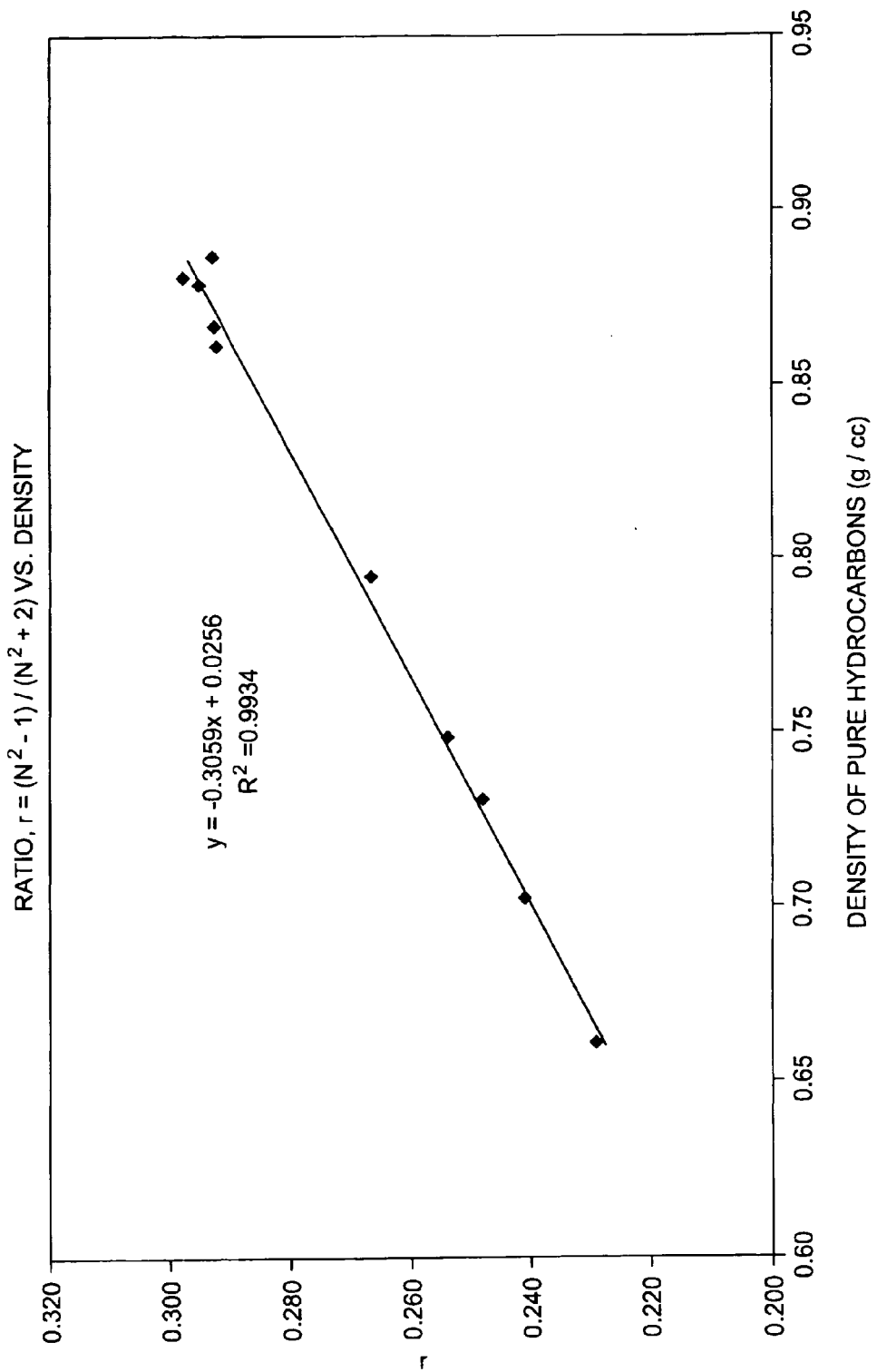
FIG. 6 is a graph showing the Clausius-Mossotti ratio $(n^2-1)/(n^2+2)$ versus density (g/cc) for a diverse group of ten pure hydrocarbons (hexane, octane, decane, dodecane, docosane, benzene, toluene, o-xylene, m-xylene, and p-xylene). These data are taken from the open literature (CRC Handbook of Chemistry and Physics, $50^{th}$ Edition, 1969)

FIG. 6 is a graph showing the Clausius-Mossotti ratio $(n^2-1)/(n^2+2)$ versus density (g/cc) for a diverse group of ten pure hydrocarbons (hexane, octane, decane, dodecane, docosane, benzene, toluene, o-xylene, m-xylene, and p-xylene). These data are taken from the open literature (CRC Handbook of Chemistry and Physics, $50^{th}$ Edition, 1969).

Figure 7:
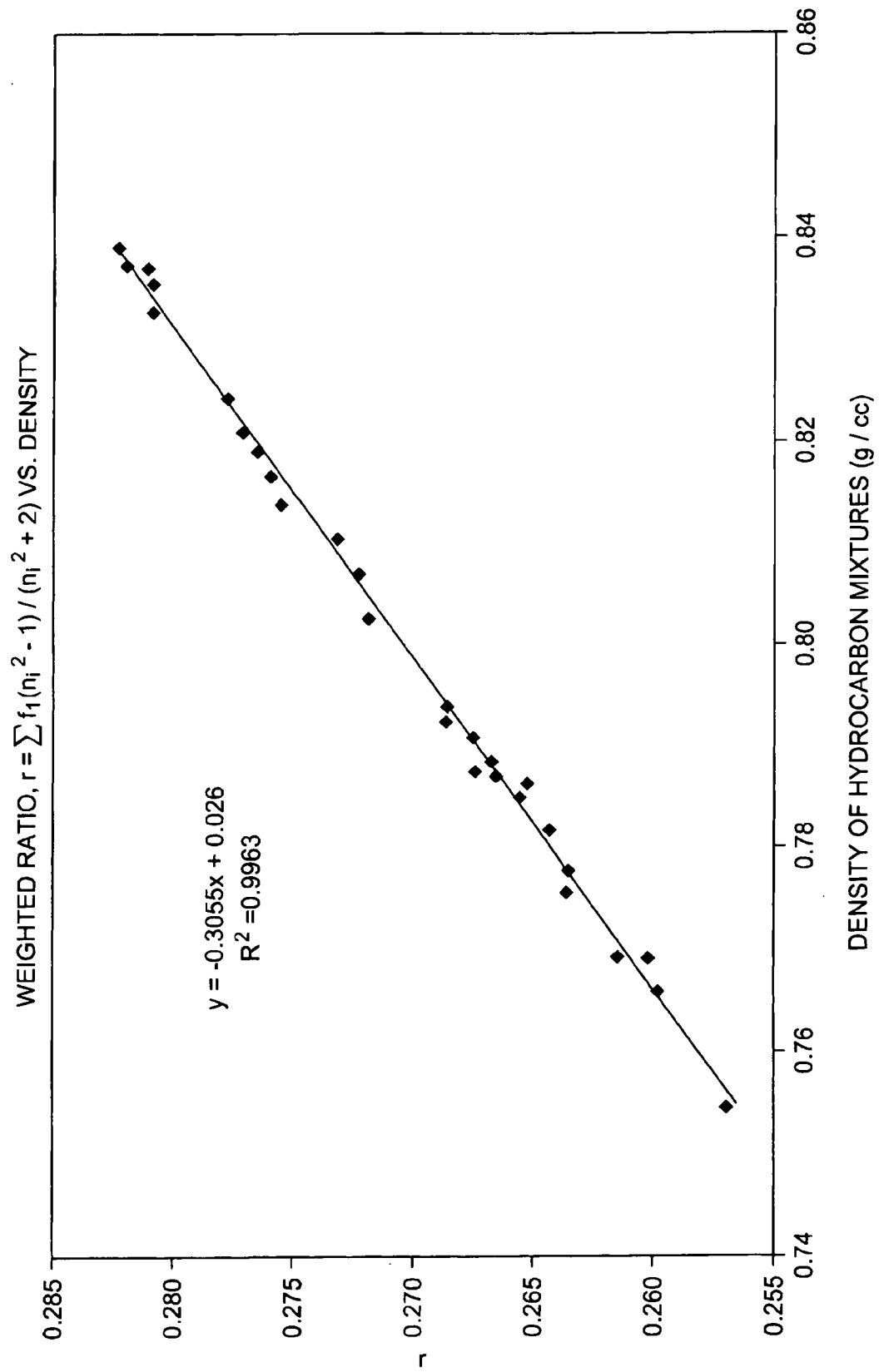
FIG. 7 is a graph showing the volumetrically weighted sum of each individual component's Clausius-Mossotti ratios versus the mixture's density (g/cc) for random synthetic mixtures of these ten pure hydrocarbons. Note that the best-fit slope and intercept is essentially the same for mixtures as it had been for pure components.

FIG. 7 is a graph showing the volumetrically weighted sum of each individual component's Clausius-Mossotti ratios versus the mixture's density (g/cc) for random synthetic mixtures of these ten pure hydrocarbons. Note that the best-fit slope and intercept is essentially the same for mixtures as it had been for pure components.

Figure 8:
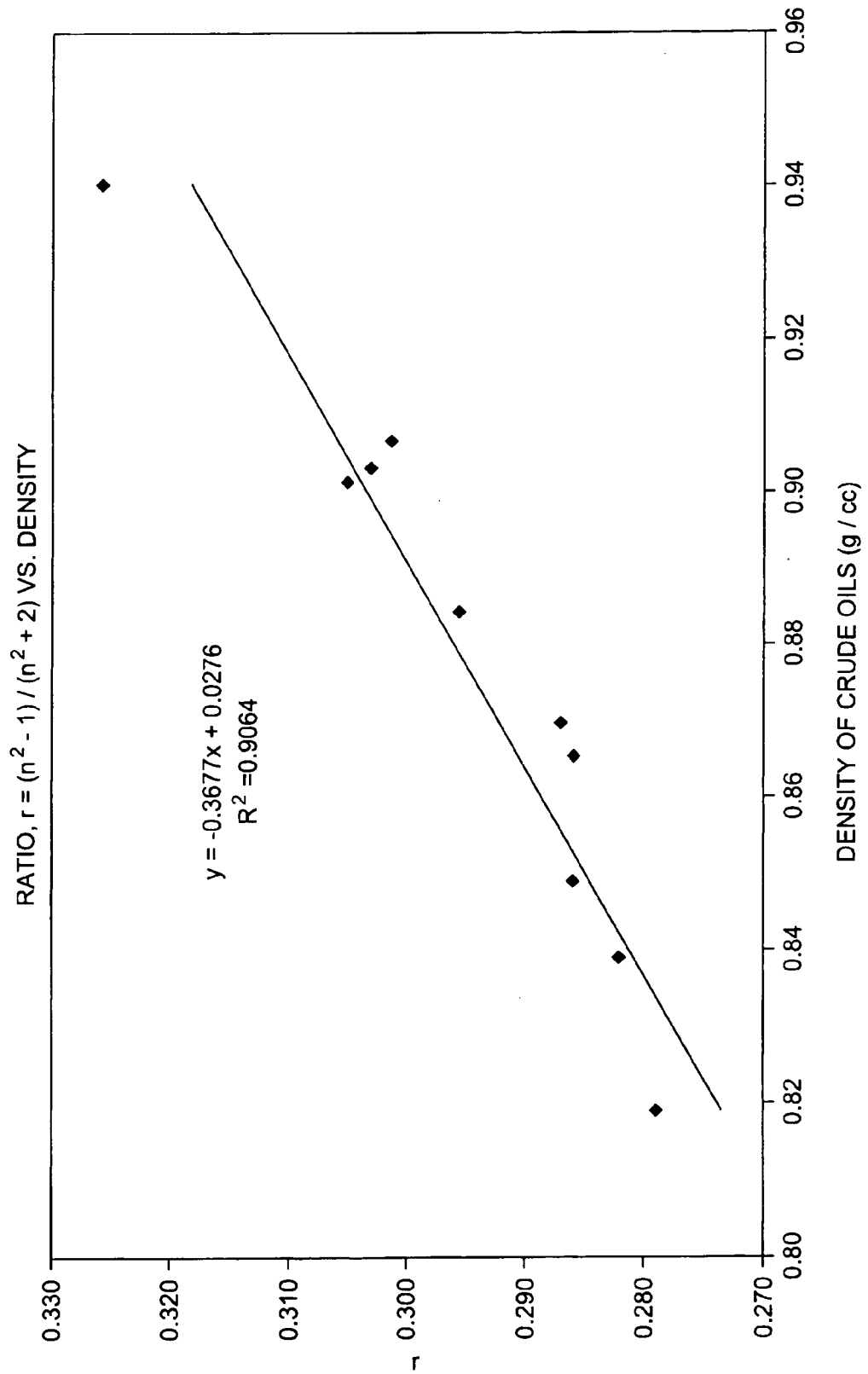
FIG. 8 is a graph showing the Clausius-Mossotti ratio $(n^2-1)/(n^2+2)$ versus density (g/cc) for a group of ten crude oils that ranged from 19° to 41° API. Note that the best-fit slope and intercept for these highly complex mixtures (crude oils) is very close to the values found for pure hydrocarbons and their mixtures, which suggests a nearly universal relationship between the Clausius-Mossotti ratio and density. These data are taken from publically available literature (Table I of Buckley, et. al, Paper 61f of 2nd International Symposium on Thermodynamics of Heavy Oils and Asphaltenes, Houston, Mar. 9–13, 1997) after excluding one outlier (the Oklahoma crude)
Figure 9:
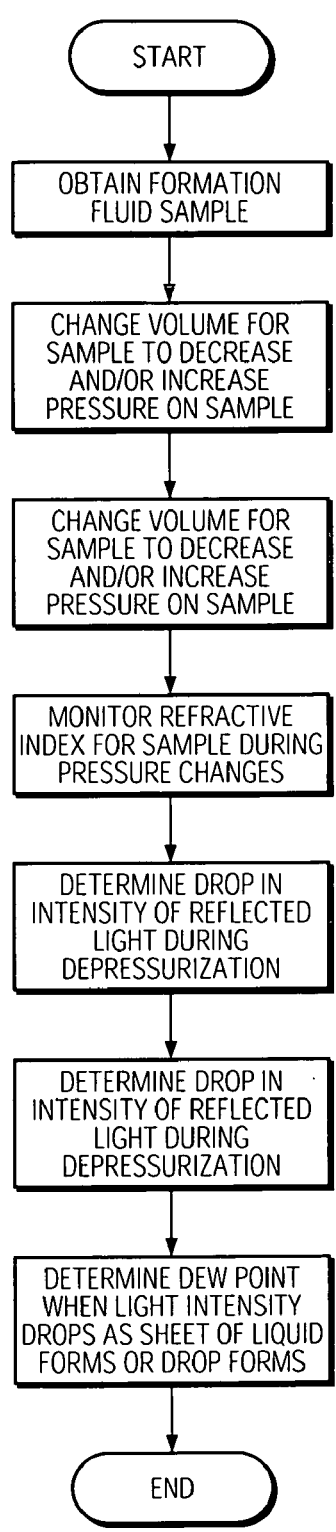
FIG. 9 is an illustration showing the process steps to determine dew point when light intensity drops as sheet of liquid forms or drops form.
Figure 10:
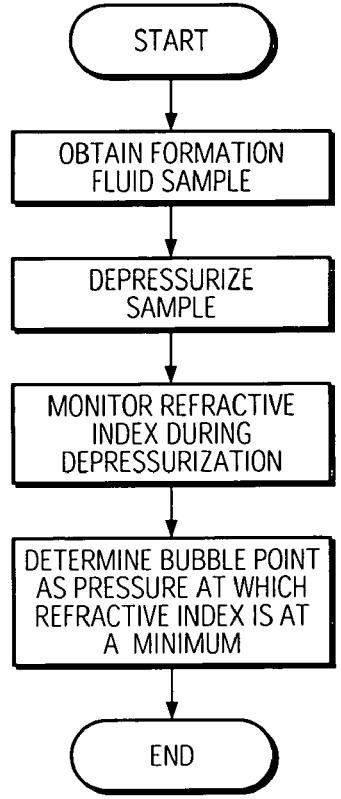
FIG. 10 is an illustration showing the process steps to determine bubble point for the pressure at which refractive index is at a minimum.
Figure 11:
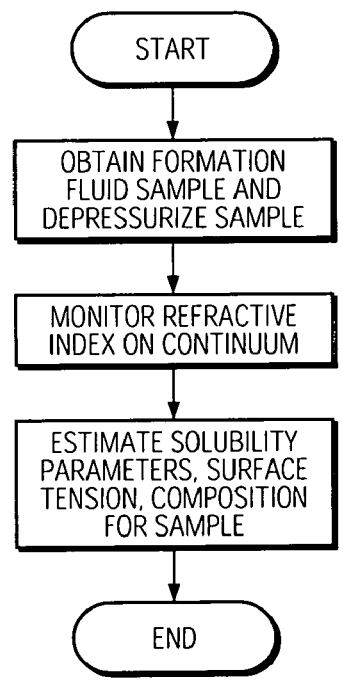
FIG. 11 is an illustration showing the process steps to estimate solubility parameters, surface tension, and composition for sample.
Figure 12:
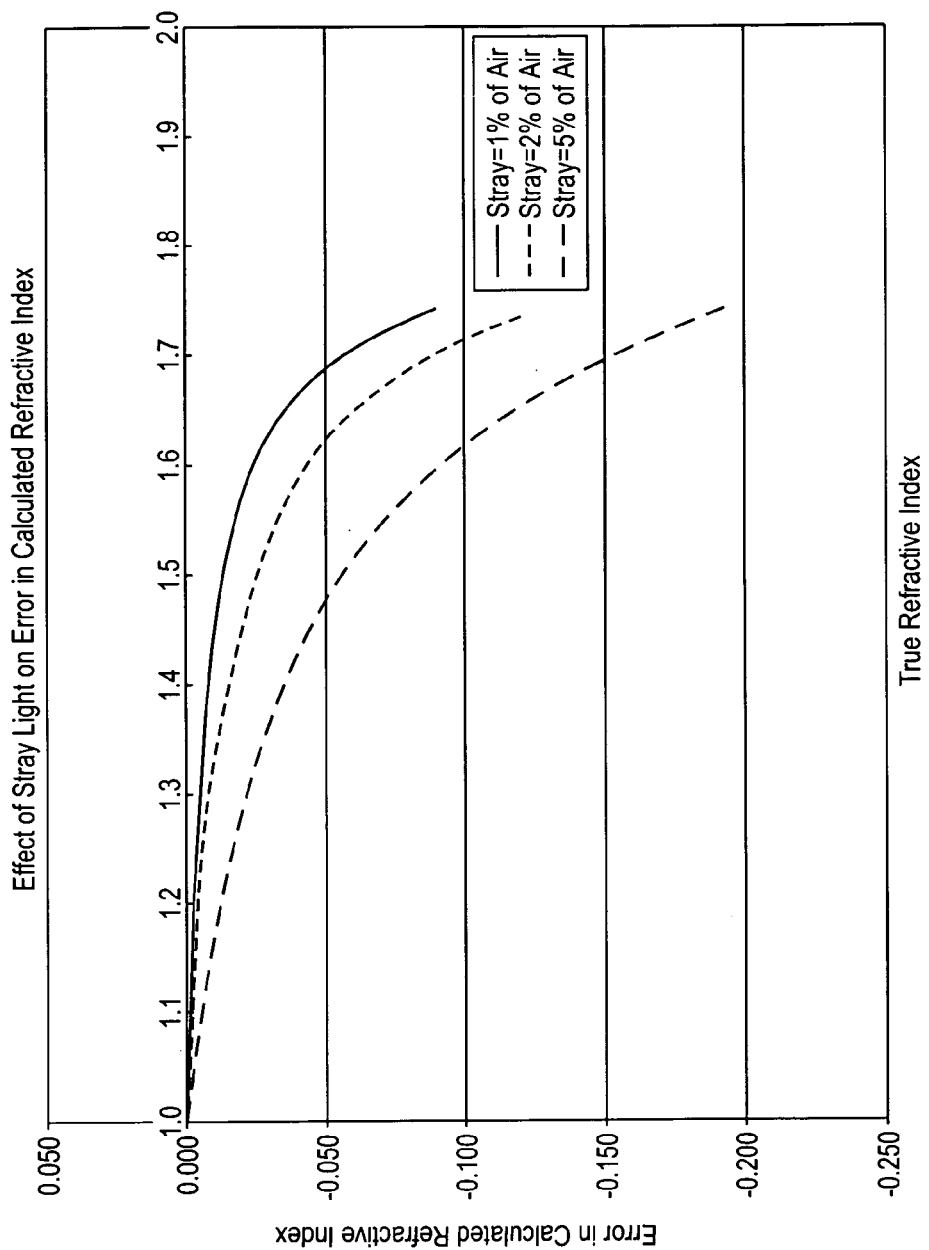
FIG. 12 shows the effect of stray light on error in the calculated refractive index.

The present invention enables measurement of a continuous refractive index downhole. It combines this measurement with an estimated molar mass, specific gravity, or boiling point, which are derived from a database of historical values for the region, inferred from experience in a particular geographic area and depth, inferred from refractive index, or measured by completely independent means. For example, the downhole specific gravity can be obtained from the gradient (slope of pressure versus depth) of a series of RCI pressure measurements at different depths in the well. Alternatively, as illustrated in FIG. 8, the specific gravity can be estimated from the refractive index itself.

Known downhole refractometers measure in 8 steps so they can only tell the user to which of these eight steps the refractive index belongs. That is, an eight-step device can only report the refractive index range (lower and upper limits of one of the eight steps) of the fluid rather than the refractive index itself.

The preferred downhole refractometer of the present invention measures refractive index along a continuum rather than in steps. Therefore, the measured refractive index enables estimation of other useful downhole properties, such as bubble point pressure, surface tension, and solubility parameters.

A plot of refractive index versus fluid pressure has its minimum at the fluid's bubble point pressure. For example, it could change from 1.47 (when the fluid is above or below the bubble point) to a minimum at 1.43 (at the bubble point). Therefore, the present invention provides an expandable sample chamber formed by channel 304, valve 340 and piston 341 to reduce the pressure downhole while measuring refractive index, using the refractometer of the present invention to determine the bubble point pressure. (Buckley, et. al, Paper 61f of 2nd International Symposium on Thermodynamics of Heavy Oils and Asphaltenes, Houston, Mar. 9–13, 1997). Expandable sample chambers to reduce pressure below the bubble point are well known in the art as disclosed in U.S. Pat. No. 6,218,662.

The parameter $Rm=(n^2-1)/[(n^2+2)\,\rho]$ represents the fraction of total volume occupied by the molecules and is a very useful parameter in predicting many physical and thermodynamic properties (Riazi M. R., Daubert T. E., "Characterization Parameters for Petroleum Fractions", Industrial and Engineering Chemistry Research, U.S.A., Vol.26, Pages 755–759, 1987). In this formula, $(n^2-1)/(n^2+2)$ is the volume occupied by the molecules per mole and $\rho$ is the number of moles (not grams) per unit volume. The parameter Rm along with other parameters can be used to estimate surface tension, bubble point, and in flash calculations (Escobedo, J. and Mansoori, G. A., Surface Tension Prediction for Liquid Mixtures, AIChE Journal, Vol. 44, No. 10, pp. 2324–2332, 1998).

The expression $(n^2-1)/(n^2+2)^{3/4}$ is proportional to the solubility parameter and can be used to estimate the polarizability of the mixture and relative fraction of aromatics versus aliphatics (Buckley, et. al, "Asphaltene Precipitation and Solvent Properties of Crude Oils", Pet. Sci. Tech., Vol. 16, No. 3–4, p. 251, 1998).

Thermodynamic and physical properties of petroleum fractions and products are important in the appropriate design and operation of equipment in petroleum production, processing and transportation. The estimation of formation fluid properties has been discussed in general as shown in the following excerpt from the abstract of a paper by Mohammad R. Riazi* and Yousef A. Roomi, which was entitled, "Minimum Lab. Data To Measure Fluid Properties", discusses the estimation of most all formation fluid properties from molar mass, specific gravity and refractive index and was presented at the 50th Canadian Chemical Engineering Conference (CSChE 2000), Montreal, Canada, Oct. 15–18, 2000. (See also, Industrial & Engineering Chemistry Research (Issue 8, 2001). Riazi, M. R. and Y. Roomi, "Use of Refractive Index in Estimating Thermophysical Properties of Hydrocarbon Mixtures", Accepted for publication in Industrial & Engineering Chemistry Research, American Chemical Society, January 2001).

Heat capacity, thermal conductivity, viscosity and density of a petroleum fraction are needed in design and operation of a heat exchanger unit in a refinery. Knowledge of the amount of benzene, aromatic and sulfur content of a petroleum product is important in determination of the quality of a petroleum fuel such as gasoline or gas oil. Experimental determination of all these properties for every petroleum mixture under different conditions is expensive and time consuming. By only measuring three basic properties almost every other property can be estimated with a good degree of accuracy. These three basic properties are molar mass, specific gravity and refractive index at 20 C. In cases that molar mass is not available, boiling point (distillation data) along with specific gravity and refractive index may be used to estimate various thermodynamic and physical properties. Petroleum fractions and products are mixtures of many hydrocarbon compounds from different groups. These compounds are non-polar and the main intermolecular force is the London dispersion force determined from polarizability, which is defined in terms of refractive index. Refractive index is an easily measurable property in a laboratory. With the knowledge of refractive index, density and molar mass one can accurately determine the amount of paraffins, naphthenes, monoaromatics, polyaromatics and sulfur in a petroleum fraction. Through these parameters many physical properties such as critical properties, equations of state parameters, viscosity, thermal conductivity, diffusivity, heat capacity and heat of vaporization can be estimated with an accuracy of 1–2% from experimental data. Many physical and thermodynamic properties of complex petroleum mixtures can be determined from very few parameters that can be measured.

Thus, utilizing the present invention to determine the refractive index of a formation sample, and providing the molar mass and specific gravity one can accurately determine the amount of paraffins, naphthenes, monoaromatics, polyaromatics and sulfur in a petroleum fraction. Through these parameters many physical properties such as critical properties, equations of state parameters, viscosity, thermal conductivity, diffusivity, heat capacity and heat of vaporization can be estimated.

The foregoing example of a preferred embodiment is intended for purposes of explanation and not intended to limit the scope of the invention, which is defined by the following claims.

What is claimed is:

1. An apparatus for determining an index of refraction of a fluid downhole, the apparatus comprising:
 a light source which directs light through a first optical transmission device to a substantially flat window adjacent to the fluid at a substantially normal angle of incidence to the window and the fluid wherein substantially all of the incident light enters the fluid;
 a second optical transmission device inclined with respect to the first optical transmission device which collects light reflected at an angle substantially equal to the substantially normal angle of incidence from the fluid; and
 an analysis system which measures intensity of the light collected from the fluid to determine the index of refraction of the fluid.

2. The apparatus of claim 1, further comprising:
 an interface between the fluid and the window and;
 a region of investigation associated with the interface from which the reflected light is reflected.

3. The apparatus of claim 1, further comprising:
 a stray light reduction device which reduces stray light entering the analysis system.

4. The apparatus of claim 2 further comprising a, stray light reduction device that includes a non reflective material absorbing light passing through the fluid to prevent back reflections from entering the formation fluid from outside the region of investigation.

5. The apparatus of claim 3, wherein the stray light reduction device comprises a black matte coating.

6. The apparatus of claim 3, wherein the stray light reduction device further comprises a spiral pattern surrounding the first and second optical transmission devices.

7. The apparatus of claim 1, wherein the light source is placed in a black chrome plated housing.

8. The apparatus of claim 1, further comprising:
 an optical filter which absorbs a selected wavelength of light from the collected light before the analysis system measures the intensity of the light collected.

9. The apparatus of claim 8, wherein the selected wavelength of light is approximately 1740 nm.

10. A system for analyzing a fluid downhole comprising:
 a downhole tool deployable down a wellbore, the downhole tool including an apparatus for defining an index of refraction of the fluid, wherein the apparatus further comprises a light source which directs light through a first optical transmission device to a substantially flat window adjacent to the fluid at a substantially normal angle of incidence to the window and the fluid wherein substantially all of the incident light enters the fluid;
 a second optical transmission device inclined with respect to the first optical transmission device which collects light reflected at an angle substantially equal to the substantially normal angle of incidence; and
 an analysis system which measures intensity of the light collected from the fluid to determine the index of refraction of the downhole fluid.

11. The system of claim 10, further comprising:
 an interface between the fluid and the window; and a region of investigation associated with the light collected from the downhole fluid from which the reflected light is reflected.

12. They system of claim 11, further comprising a stray light reduction device that includes a non reflective material intercepting light material absorbing light passing through the fluid to prevent back reflections from entering the fluid from outside the region of investigation.

13. The system of claim 10, further comprising:
 a stray light reduction device which reduces stray light entering the analysis system.

14. The system of claim 13, wherein the light source is placed in a black chrome plated housing.

15. The system of claim 13, wherein the stray light reduction device comprises a black matte coating.

16. The system of claim 13,
 wherein the stray light reduction device comprises a spiral pattern surrounding the first and second optical transmission devices.

17. The system of claim 10, further comprising:
 an optical filter which absorbs a selected wavelength of light from the collected light before the analysis system measures the intensity of the collected light.

18. The system of claim 17, wherein the selected wavelength of light is approximately 1740 nm.

19. A method for determining an index of refraction of a fluid downhole comprising:
 directing light through a first optical transmission device to a substantially flat window adjacent to the downhole fluid at a substantially normal angle of incidence to the window and the downhole fluid wherein substantially all of the incident light enters the fluid;
 collecting light reflected at an angle equal to the substantially normal angle of incidence from the fluid in a second optical transmission device inclined with respect to the first optical transmission device; and
 measuring intensity of the light collected from the fluid in an analysis system to determine the index of refraction of the fluid.

20. The method of claim 19, wherein measuring the light includes measuring light from a region of investigation associated with the light collected from the downhole fluid.

21. The method of claim 19, further comprising:
 reducing stray light entering the analysis system.

22. The method of claim 19, further comprising:
 reducing stray light includes absorbing light passing through the fluid to prevent back reflections from entering the fluid from outside of the region of investigation.

23. The method of claim 22,
 wherein reducing stray light further comprises surrounding the first and second optical transmission device with a spiral pattern.

24. The method of claim 19, further comprising:
 reducing stray light by placing a light source in a black chrome plated housing.

25. The method of claim 24, wherein reducing stray light further comprises applying a black matte coating to the housing.

26. The method of claim 19, further comprising:
 absorbing a selected wavelength of light in an optical filter before the electronic analysis system measures the intensity of the light collected.

27. The method of claim 26, wherein the selected wavelength of light is approximately 1740 nanometers.

* * * * *